United States Patent
Trieu (10) Patent No.: US 9,414,864 B2
(45) Date of Patent: Aug. 16, 2016

(54) ANTERIOR SPINAL PLATE WITH PREFORMED DRUG-ELUTING DEVICE AFFIXED THERETO

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1525 days.

(21) Appl. No.: 12/409,089

(22) Filed: Apr. 15, 2009

(65) Prior Publication Data

US 2010/0268282 A1    Oct. 21, 2010

(51) Int. Cl.

| | | |
|---|---|---|
| *A61B 17/80* | (2006.01) | |
| *A61B 17/70* | (2006.01) | |
| *A61K 9/00* | (2006.01) | |
| *A61K 47/24* | (2006.01) | |
| *A61K 47/32* | (2006.01) | |
| *A61K 47/34* | (2006.01) | |
| *A61B 17/00* | (2006.01) | |

(52) U.S. Cl.
CPC ......... *A61B 17/7059* (2013.01); *A61B 17/8042* (2013.01); *A61K 9/0024* (2013.01); *A61K 47/24* (2013.01); *A61K 47/32* (2013.01); *A61K 47/34* (2013.01); *A61B 2017/00004* (2013.01); *A61B 2017/00951* (2013.01)

(58) Field of Classification Search
CPC .................. A61F 2002/4435; A61F 2/30767; A61B 17/80; A61B 17/7059; A61L 27/365; A61L 2300/61
USPC .................................... 606/70, 280, 295, 298
See application file for complete search history.

(56) References Cited

U.S. PATENT DOCUMENTS

| | | |
|---|---|---|
| 4,006,741 A | 2/1977 | Arluck |
| 4,136,686 A | 1/1979 | Arluck |
| 4,286,586 A | 9/1981 | Potts |
| 5,061,281 A | 10/1991 | Mares et al. |
| 5,061,286 A | 10/1991 | Lyle |
| 5,217,493 A | 6/1993 | Raad et al. |
| 5,344,457 A | 9/1994 | Pilliar et al. |
| 5,458,653 A | 10/1995 | Davidson |
| 5,609,629 A | 3/1997 | Fearnot et al. |
| 5,624,704 A | 4/1997 | Darouiche et al. |
| 5,660,854 A | 8/1997 | Haynes et al. |
| 5,753,251 A | 5/1998 | Burrell et al. |
| 5,755,759 A | 5/1998 | Cogan |
| 5,824,049 A | 10/1998 | Ragheb et al. |
| 5,853,745 A | 12/1998 | Darouiche |
| 5,874,101 A | 2/1999 | Zhong et al. |
| 5,877,224 A | 3/1999 | Brocchini et al. |
| 5,879,697 A | 3/1999 | Ding et al. |
| 5,902,283 A | 5/1999 | Darouiche et al. |
| 5,951,558 A | 9/1999 | Fiz |
| 5,980,973 A | 11/1999 | Onyekaba et al. |
| 6,015,816 A | 1/2000 | Kostyniak et al. |
| 6,033,582 A | 3/2000 | Lee et al. |
| 6,042,875 A | 3/2000 | Ding et al. |
| 6,077,076 A | 6/2000 | Comfort |
| 6,096,070 A | 8/2000 | Ragheb et al. |
| 6,096,080 A | 8/2000 | Nicholson et al. |
| 6,153,212 A | 11/2000 | Mao et al. |
| 6,166,173 A | 12/2000 | Mao et al. |

(Continued)

*Primary Examiner* — Brian Pellegrino
(74) *Attorney, Agent, or Firm* — Sorell Lenna & Schmidt LLP (57) ABSTRACT

An anterior spinal plate has affixed to at least a portion of a surface thereof at least one preformed drug-eluting device fabricated from a drug-eluting matrix containing at least one elutable drug.

17 Claims, 2 Drawing Sheets

(56) References Cited

U.S. PATENT DOCUMENTS

| | | |
|---|---|---|
| 6,228,393 B1 | 5/2001 | DiCosmo et al. |
| 6,238,687 B1 | 5/2001 | Mao et al. |
| 6,299,604 B1 | 10/2001 | Ragheb et al. |
| 6,322,797 B1 | 11/2001 | Mao et al. |
| RE37,479 E | 12/2001 | Kuslich |
| 6,335,029 B1 | 1/2002 | Kamath et al. |
| 6,428,579 B1 | 8/2002 | Valentini |
| 6,443,987 B1 | 9/2002 | Bryan |
| 6,478,822 B1 | 11/2002 | Leroux et al. |
| 6,527,801 B1 | 3/2003 | Dutta |
| 6,534,197 B2 | 3/2003 | Noda et al. |
| 6,558,686 B1 | 5/2003 | Darouiche |
| 6,558,734 B2 | 5/2003 | Koulik et al. |
| 6,559,119 B1 | 5/2003 | Burgess et al. |
| 6,582,715 B1 | 6/2003 | Barry et al. |
| 6,589,546 B2 | 7/2003 | Kamath et al. |
| 6,607,530 B1 | 8/2003 | Carl et al. |
| 6,652,525 B1 | 11/2003 | Assaker et al. |
| 6,692,498 B1 | 2/2004 | Niiranen et al. |
| 6,719,795 B1 | 4/2004 | Cornwall et al. |
| 6,730,064 B2 | 5/2004 | Ragheb et al. |
| 6,733,503 B2 | 5/2004 | Layrolle et al. |
| 6,736,815 B2 | 5/2004 | Ginn |
| 6,755,828 B2 | 6/2004 | Shevtsov et al. |
| 6,770,288 B2 | 8/2004 | Duirs |
| 6,770,729 B2 | 8/2004 | Van Antwerp |
| 6,774,278 B1 | 8/2004 | Ragheb et al. |
| 6,808,738 B2 | 10/2004 | DiTizio et al. |
| 6,843,804 B2 | 1/2005 | Bryan |
| 6,843,807 B1 | 1/2005 | Boyce et al. |
| 6,899,713 B2 | 5/2005 | Shaolian et al. |
| 6,902,743 B1 | 6/2005 | Setterstrom et al. |
| 6,919,100 B2 | 7/2005 | Narayanan |
| 6,921,811 B2 | 7/2005 | Zamora et al. |
| 6,923,811 B1 | 8/2005 | Carl et al. |
| 6,951,561 B2 | 10/2005 | Warren et al. |
| 6,964,667 B2 | 11/2005 | Sholian et al. |
| 6,986,771 B2 | 1/2006 | Paul et al. |
| 6,989,011 B2 | 1/2006 | Paul et al. |
| 6,991,802 B1 | 1/2006 | Ahola et al. |
| 6,994,883 B2 | 2/2006 | Layrolle et al. |
| 6,998,134 B2 | 2/2006 | Schmidmaier et al. |
| 7,052,497 B2 | 5/2006 | Sherman et al. |
| 7,056,533 B2 | 6/2006 | Chudzik et al. |
| 7,056,550 B2 | 6/2006 | Davila et al. |
| 7,077,859 B2 | 7/2006 | Sirhan et al. |
| 7,090,668 B1 | 8/2006 | U et al. |
| 7,101,840 B2 | 9/2006 | Brocchini et al. |
| 7,105,018 B1 | 9/2006 | Yip et al. |
| 7,105,023 B2 | 9/2006 | Eckman |
| 7,144,422 B1 | 12/2006 | Rao |
| 7,157,096 B2 | 1/2007 | Zhang et al. |
| 7,163,561 B2 | 1/2007 | Michelson |
| 7,169,404 B2 | 1/2007 | Hossainary et al. |
| 7,175,611 B2 | 2/2007 | Mitchnick |
| 7,182,783 B2 | 2/2007 | Trieu |
| 7,189,409 B2 | 3/2007 | Pirhonen et al. |
| 7,192,445 B2 | 3/2007 | Ellingsen et al. |
| 7,192,604 B2 | 3/2007 | Brown et al. |
| 7,238,203 B2 | 7/2007 | Bagga et al. |
| 7,238,363 B2 | 7/2007 | Mansouri et al. |
| 7,279,175 B2 | 10/2007 | Chen et al. |
| 7,303,814 B2 | 12/2007 | Lamberti |
| 7,309,338 B2 | 12/2007 | Cragg |
| 7,314,857 B2 | 1/2008 | Madhyastha |
| 7,320,798 B2 | 1/2008 | Zhang et al. |
| 7,320,799 B2 | 1/2008 | Zhang et al. |
| 7,335,205 B2 | 2/2008 | Aeschlimann et al. |
| 7,378,106 B2 | 5/2008 | Hossainy et al. |
| 7,410,502 B2 | 8/2008 | Ellingsen et al. |
| 7,410,665 B2 | 8/2008 | Ragheb et al. |
| 7,413,574 B2 | 8/2008 | Yip et al. |
| 7,413,806 B2 | 8/2008 | Ong et al. |
| 7,416,558 B2 | 8/2008 | Yip et al. |
| 7,431,734 B2 | 10/2008 | Danoff et al. |
| 7,445,628 B2 | 11/2008 | Ragheb et al. |
| 7,470,283 B2 | 12/2008 | Dutta |
| 7,717,946 B2 * | 5/2010 | von Oepen et al. ........... 606/298 |
| 2002/0090398 A1 | 7/2002 | Dunn et al. |
| 2002/0123750 A1* | 9/2002 | Eisermann et al. ............ 606/69 |
| 2002/0147496 A1 | 10/2002 | Belef et al. |
| 2002/0147497 A1 | 10/2002 | Belef et al. |
| 2002/0188037 A1 | 12/2002 | Chudzik et al. |
| 2003/0039689 A1 | 2/2003 | Chen et al. |
| 2003/0045937 A1 | 3/2003 | Ginn |
| 2003/0099762 A1 | 5/2003 | Zhang et al. |
| 2003/0125739 A1 | 7/2003 | Bagga et al. |
| 2003/0139814 A1 | 7/2003 | Bryan |
| 2003/0229319 A1 | 12/2003 | Mitchnick |
| 2004/0030342 A1 | 2/2004 | Trieu et al. |
| 2004/0043052 A1 | 3/2004 | Hunter et al. |
| 2004/0047909 A1 | 3/2004 | Ragheb et al. |
| 2004/0054414 A1* | 3/2004 | Trieu et al. ................. 623/17.16 |
| 2004/0059333 A1 | 3/2004 | Carl et al. |
| 2004/0083002 A1 | 4/2004 | Belef et al. |
| 2004/0127906 A1 | 7/2004 | Culbert et al. |
| 2004/0158246 A1 | 8/2004 | Assaker et al. |
| 2004/0158248 A1 | 8/2004 | Ginn |
| 2004/0172132 A1 | 9/2004 | Ginn |
| 2004/0220571 A1 | 11/2004 | Assaker et al. |
| 2004/0236327 A1 | 11/2004 | Paul et al. |
| 2004/0236328 A1 | 11/2004 | Paul et al. |
| 2005/0019404 A1 | 1/2005 | Sung et al. |
| 2005/0027360 A1 | 2/2005 | Webb et al. |
| 2005/0031666 A1 | 2/2005 | Trieu |
| 2005/0033289 A1 | 2/2005 | Warren et al. |
| 2005/0064005 A1* | 3/2005 | Dinh et al. ..................... 424/422 |
| 2005/0079199 A1 | 4/2005 | Heruth et al. |
| 2005/0079200 A1 | 4/2005 | Rathenow et al. |
| 2005/0220837 A1 | 10/2005 | Disegi et al. |
| 2005/0240076 A1 | 10/2005 | Neisz et al. |
| 2005/0244459 A1 | 11/2005 | Dewitt et al. |
| 2005/0255142 A1 | 11/2005 | Chudzik et al. |
| 2005/0271694 A1 | 12/2005 | Mansouri et al. |
| 2005/0276841 A1 | 12/2005 | Davis et al. |
| 2006/0015105 A1 | 1/2006 | Warren et al. |
| 2006/0034891 A1 | 2/2006 | Lawin et al. |
| 2006/0039946 A1 | 2/2006 | Heruth et al. |
| 2006/0041259 A1 | 2/2006 | Paul et al. |
| 2006/0047341 A1 | 3/2006 | Trieu |
| 2006/0051392 A1 | 3/2006 | Heruth et al. |
| 2006/0057277 A1 | 3/2006 | Chappa |
| 2006/0089722 A1 | 4/2006 | Montevecchi et al. |
| 2006/0093646 A1 | 5/2006 | Cima et al. |
| 2006/0115457 A1 | 6/2006 | Hnojewyj |
| 2006/0121083 A1 | 6/2006 | Mor |
| 2006/0127438 A1 | 6/2006 | Hunter et al. |
| 2006/0198903 A1 | 9/2006 | Storey et al. |
| 2006/0204537 A1 | 9/2006 | Ratner et al. |
| 2006/0229615 A1 | 10/2006 | Abdou |
| 2006/0235530 A1 | 10/2006 | Shelokov |
| 2007/0016163 A1 | 1/2007 | Santini et al. |
| 2007/0050010 A1 | 3/2007 | Bates et al. |
| 2007/0071789 A1 | 3/2007 | Panteildis et al. |
| 2007/0104758 A1 | 5/2007 | Hamilton et al. |
| 2007/0116734 A1 | 5/2007 | Akash |
| 2007/0118132 A1 | 5/2007 | Culbert et al. |
| 2007/0123868 A1 | 5/2007 | Culbert et al. |
| 2007/0125247 A1 | 6/2007 | Kunstmann et al. |
| 2007/0134827 A1 | 6/2007 | Troxel et al. |
| 2007/0141100 A1 | 6/2007 | Sung |
| 2007/0154621 A1 | 7/2007 | Road |
| 2007/0168012 A1 | 7/2007 | Ragheb et al. |
| 2007/0212387 A1 | 9/2007 | Patravale et al. |
| 2007/0218102 A1 | 9/2007 | Chudzik et al. |
| 2007/0224162 A1 | 9/2007 | Roby et al. |
| 2007/0265622 A1 | 11/2007 | Aeschlimann et al. |
| 2007/0270812 A1 | 11/2007 | Peckman |
| 2007/0270858 A1 | 11/2007 | Trieu et al. |
| 2007/0287129 A1 | 12/2007 | Ihde |
| 2007/0293948 A1 | 12/2007 | Bagga et al. |
| 2007/0299520 A1 | 12/2007 | Trieu et al. |
| 2007/0299535 A1 | 12/2007 | Ihde |
| 2008/0008988 A1 | 1/2008 | McKay et al. |

(56) References Cited

U.S. PATENT DOCUMENTS

| | | |
|---|---|---|
| 2008/0015578 A1 | 1/2008 | Erickson et al. |
| 2008/0038316 A1 | 2/2008 | Wong |
| 2008/0045961 A1 | 2/2008 | Aeschlimann et al. |
| 2008/0063693 A1 | 3/2008 | Cook et al. |
| 2008/0089952 A1 | 4/2008 | Hunter et al. |
| 2008/0107711 A1 | 5/2008 | Shelokov |
| 2008/0108824 A1 | 5/2008 | Isch et al. |
| 2008/0113000 A1 | 5/2008 | Hunter et al. |
| 2008/0132992 A1 | 6/2008 | Bates et al. |
| 2008/0145514 A1 | 6/2008 | Hunter et al. |
| 2008/0152784 A1 | 6/2008 | Stenzel |
| 2008/0154311 A1 | 6/2008 | Staeubli |
| 2008/0154368 A1 | 6/2008 | Justis et al. |
| 2008/0154373 A1 | 6/2008 | Protopsaltis et al. |
| 2008/0161907 A1 | 7/2008 | Chen et al. |
| 2008/0183152 A1 | 7/2008 | Raad et al. |
| 2008/0220041 A1 | 9/2008 | Brito et al. |
| 2008/0221623 A1 | 9/2008 | Gooch |
| 2008/0221624 A1 | 9/2008 | Gooch |
| 2008/0241217 A1 | 10/2008 | Hunter et al. |
| 2008/0269742 A1 | 10/2008 | Levy et al. |
| 2008/0269810 A1 | 10/2008 | Zhang et al. |
| 2008/0299102 A1 | 12/2008 | Marenzi et al. |

\* cited by examiner

ANTERIOR SPINAL PLATE WITH PREFORMED DRUG-ELUTING DEVICE AFFIXED THERETO

BACKGROUND OF THE INVENTION

This invention relates generally to orthopedic implants possessing drug-eluting or drug-diffusing capability. More particularly, the invention is for an anterior spinal plate having such capability.

Numerous orthopedic implants, including spinal implants such as anterior spinal plates, are known to possess adherent coatings, layers or films containing one or more drugs, e.g., medicaments, therapeutics, biologicals or other bioactive substances, etc., such as antimicrobials, antibacterials, antibiotics, antifungicides, anti-inflammatories, and the like. Following the installation of such an implant in the body, the drug(s) present in the coating elutes therefrom over time into the region of surrounding tissue to achieve the desired drug actions(s).

One of the problems encountered in the manufacture of an orthopedic implant possessing a drug-eluting coating involves the sterilization of such a device. The more economical methods of sterilization utilize steam under pressure, e.g., as produced in an autoclave. While such sterilization methods are known to be highly effective, they are subject to a major disadvantage where thermally sensitive drugs are concerned and therefore are of limited use. While the conventional use of sterilizing radiation or a sterilant gas such as ethylene oxide can reduce the risk of damaging or partially to completely inactivating the drug component(s) present in the coating component of an orthopedic implant, such sterilization methods are relatively expensive. While it is possible in principle to apply a drug-containing coating to a pre-sterilized implant under sterile conditions followed by the sterile packaging of the coated implant, such an approach to providing a packaged sterile orthopedic implant, which avoids subjecting the drug(s) contained in its drug-eluting coating to thermal decomposition or deactivation, is largely an impractical one.

Therefore, what is needed is a drug-eluting cover that can be applied to an implant in vivo or in vitro where the drug-eluting cover can be sterilized separately from the implant and configured to fit a variety of implants. The present invention provides such a device and is described in further detail below.

SUMMARY OF THE INVENTION

In accordance with the present invention, there is provided an anterior spinal plate having affixed to at least a portion of the surface thereof at least one preformed drug-eluting device fabricated from drug-eluting biocompatible matrix containing at least one elutable drug. Useful bioresorbable drug-eluting matrices include hydrogels, and polymers such as poly(L-lactic acid), poly(glycolic acid), poly(lactide-co-glycolide), polydioxanone, polyorthoesters, polyanhydrides, and the like. For example, such polymers include but are not limited to a polyvinyl alcohol, a polyacrylic acid, a polyarylamide, a poly(acrylonitrile-acrylic acid), a polyurethane, a polyethylene glycol, a poly(N-vinyl-2-pyrrolidone), a gelatin, a collagen, a polysaccharide, a cellulose, and combinations thereof. The present invention can be made from hydrogels either impregnated with and/or coated with antibacterial/antimicrobial agents such as silver atoms, silver ions and/or mixtures thereof. The hyrdogels of the present invention may be hydrated or unhydrated. The unhydrated hydrogels of the present invention will become hydrated either prior, during or after implantation. Once hydrated the hydrogels will increase in dimensions.

The silver metal and/or the silver comprising compounds of the present invention can be in the form of nanoparticles, particulate, powder, granules, or thin coatings ranging from the highest surface area to the least surface area. The size of the particles can range from about 10 nanometers to about 500 microns, preferably about 50 nanometers to 50 microns.

Hydrogels that can be used for the present invention may also be made non-bioresorbable by means of the process in which they are produced as well as the molecular composition. Various degrees of bioresorbablity can also be accomplished by varying the amount of cross-linking in the hydrogel.

According to a further aspect of the invention, there is provided a method for surgically installing an anterior spinal plate in a body which comprises surgically installing an anterior spinal plate in the body of a subject and affixing to at least a portion of a surface of the plate a preformed drug-eluting device containing at least one elutable drug, the affixing step being carried out immediately prior to, during or following the installing step.

The term "anterior spinal plate" shall be understood herein to include the fixation mechanisms, e.g., screws or other fasteners, by which the plate is secured to spinal bone.

The term "preformed" as it is applied to the drug-eluting device of the invention is to be understood as distinguishing the drug-eluting device from a drug-eluting coating which is manufactured upon a surface of the implant. Thus, the drug-eluting device affixed to the anterior spinal plate of the invention, in contrast to known orthopedic implants possessing a drug-eluting coating, film, or layer manufactured thereon, is not produced upon a surface of the anterior spinal plate but upon some other surface if, indeed, it is produced upon a surface of any substrate at all. It is only after the fabrication of the drug-eluting device of the invention that the device is affixed to the plate.

The term "biocompatible" as applied to the drug-eluting material from which the drug-eluting device herein is fabricated shall be understood in its ordinary art-recognized sense as describing a material exhibiting a relatively low chronic tissue response for the period that the material is present in the body of a subject into which the drug-eluting device has been implanted.

The expression "drug-eluting" shall be understood to refer to any and all mechanisms, e.g., diffusion, migration, permeation, and/or desorption by which the drug(s) incorporated in the drug-eluting material pass therefrom over time into the surrounding body tissue.

The expression "drug-eluting material" shall be understood herein to mean any natural, synthetic or semi-synthetic material capable of acquiring and retaining a desired shape or configuration and into which one or more drugs can be incorporated and from which incorporated drug(s) are capable of eluting over time.

The expression "elutable drug" shall be understood to mean any drug or combination of drugs having the ability to pass over time from the drug-eluting material in which it is incorporated into the surrounding areas of the body.

The term "drug" includes all medically useful bio-affecting and body-treating compositions.

Other than where otherwise indicated, all numbers expressing amounts of materials, concentrations, quantified properties of materials, and so forth, stated in the specification and claims are to be understood as being modified in all instances by the term "about" or "approximately."

It will also be understood that any numerical range recited herein is intended to include all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The distinction between a drug-eluting coating as utilized by heretofore known orthopedic implants and the preformed drug-eluting device of this invention is a fundamental one and is of considerable significance for addressing the sterilization problem discussed above. Thus, an anterior plate according to the present invention can be supplied to an orthopedic surgeon as two separately sterilized components, one being the anterior plate which has been sterilized by the economical autoclave method and the other being a preformed drug-eluting device which has been sterilized by some other method, e.g., the use of sterilizing radiation or sterilant gas, that does not subject the drug(s) present therein to any significant level of decomposition, denaturation or deactivation. The surgeon then has the choice of affixing the drug-eluting device to the anterior plate just prior to, during or just after installation of the anterior spinal plate in the body as the particular circumstances may require.

Another major advantage of the anterior spinal plate of the invention is that it can be assembled at the time of installation from a specific spinal anterior plate and a specific drug-eluting device which can be selected from amongst a variety of such devices, each differing in the nature and/or amounts of the drug(s) contained therein and/or the nature of the drug-eluting composition, or drug-eluting material, from which the device is fabricated thereby offering the surgeon considerable flexibility for choosing the optimal anterior spinal plate and the optimal preformed drug-eluting device for affixation thereto for a particular patient's circumstances and needs. It is far more practical to provide such flexibility of choice in the case of an in situ assembled drug-eluting anterior spinal plate as in the present invention than to provide the same number of choices for a pre-coated anterior spinal plate of the prior art. To illustrate this, consider the case where a surgeon desires to choose from among 5 different sizes, designs or configurations of anterior spinal plate and five different drugs to be eluted. In the case of the in situ assembled anterior spinal plate of the invention, the surgeon need only have on hand 5 choices of anterior plate and 5 choices of pre-formed drug-eluting device (for a total of just 10 pre-assembly units) to meet all contemplated situations. However, it would require 25 pre-coated anterior spinal plates of the prior art to provide the same total number of choices.

The foregoing scenario points to yet another advantage of the invention over the prior art, namely, it presents the surgeon with the opportunity to choose from among all suppliers' anterior spinal plates to which a preformed drug-eluting device may be affixed. The surgeon is therefore not limited to the anterior spinal plate offerings of just one or a few suppliers but has as many choices in this regard as the then-current commercial situation makes available.

BRIEF DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems, or devices, and any further applications of the principles of the invention as described herein, are contemplated as would normally occur to one skilled in the art to which the invention relates.

Anterior spinal plates and their use in the surgical treatment of spinal injuries and defects are well known in the art. The plates can be fabricated from a wide range of materials including metals, synthetic polymers, ceramics and bone. Examples of these materials include metals such as medical grade stainless steel, titanium and titanium alloys, and the like, synthetic polymers such as thermoplastic polymers, thermoset polymers, elastomers, and the like, ceramics such as pyrolytic carbon, carbon fibers, and their composites, zirconia, alumina, titanic and their composites, and the like, bone, e.g., autograft, allograft, xenograft or transgenic cortical and/or corticocancellous bone obtained, e.g., from the femur, tibia, fibula radius and/or ulna and provided as a single unit or as a composite built up from smaller bone elements and/or bone-derived particles. Anterior spinal plates come in many different sizes and configurations for installation at various cervical, thoracic and lumbar regions of the spine. Their fastener components (typically screws) aside, anterior spinal plates can be provided as a single unit or as an assemblage of two or more sub-units. Illustrative spinal plates are those described in U.S. Pat. Nos. 6,193,721; 6,206,882; 6,224,602; 6,228,085; 6,258,089; 6,342,055; 6,413,259; 6,533,786; 6,602,255; 6,602,256; 6,605,090; 6,613,053; 6,679,883; 6,755,833; 6,761,719; 7,041,105; 7,169,150; 7,186,256; 7,306,605; 7,468,069; and, 7,481,829, and U.S. patent application publications 2004/0204712; 2005/0192577; 2005/0228386; 2007/0043369; 2007/0233110; 2007/0276371; 2008/0234753; 2009/0012571; and, 2009/0024171, the entire contents of which are incorporated by reference herein.

Coating containing drug reservoirs that are distinguishable from the present invention have been described in U.S. Patent Nos. 2005/0031666; 2007/0299520; 2006/0047341; 2007/0270858; 2004/0030342; 2007/0173934, the entire contents of which are incorporated by reference herein.

Prior to, during or following the surgical installation of a selected anterior spinal plate, there is affixed to at least a portion of the surface of the anterior spinal plate, e.g., a portion of an exposed surface, at least one preformed drug-eluting device fabricated from a drug-eluting matrix and containing a drug in accordance with this invention.

The drug-eluting device and/or drug-eluting matrix can possess a planar shape, e.g., that of a square, rectangle, circle, oval, etc., or a shape which is identical to or approximates that of the surface of the anterior spinal plate to which it is to be affixed. The drug-eluting matrix can be formed from a material of homogeneous or heterogeneous composition, can possess a single layer or multiple layers (i.e., a laminate), can be rigid, flexible or semiflexible, can be stretchable (elastic) so as to engagedly fit some portion of its associated anterior spinal plate or nonstretchable (inelastic), can be porous or non-porous, can vary considerably in its average dimensions, etc.

In one embodiment of the present invention, the drug-eluting matrix and/or drug-eluting device is in the form of a planer sheet having at least one extension configured to fit within a complimentary cavity located on the surgical implant. The planer sheet having the drug-eluting matrix can be positioned so that the extension (or extensions) snap (or pressure fit) into and/or onto the surgical implant. The planer sheet may be of any geometric sizes or shapes. In this embodiment, the surface of the drug eluting matrix is in direct contact with at least one surface of the implant. Unlike the embodiment that uses an adhesive to attach the matrix to the surgical implant, in this configuration, the drug is eluted from the drug-eluting matrix towards the surgical implant as well as to the surrounding soft tissue. In other words, in this embodiment the drug passes directly to the surface of the implant so as to prevent any infections that may arise between the drug eluting layer and the surface of the spinal anterior plate. Since no contact between surfaces is absolutely perfect, gaps and/or air pockets can and will arise between the drug-eluting matrix and the surface of the anterior plate. These gaps and/or pockets can develop infections which can be prevented by use of antimicrobial/anti-infectious compounds which elute from the matrix into the pockets that may form. In addition to preventing infection in these gaps/pockets, the drug-eluting matrix also elutes into the soft tissue surrounding the implant.

In yet another embodiment, the surgical implant can be configured to have at least one locking element that allows the drug-eluting matrix of the present invention to connect thereto. In other words, the locking element on the implant is configured so as to allow fixed engagement of the drug-eluting device. This type of fixed engagement directly attaches the drug-eluting device immediately adjacent to the surface of the implant. Other variations and configurations of this locking element/drug-eluting device embodiment can include detent locking mating configurations, friction fit, pressure fit and various other configurations known in the art.

The drug-eluting device and/or drug-eluting matrix can be dimensioned and configured as desired by any suitable technique, e.g., molding, machining, die-cutting from a larger sheet or section, etc., and can be dimensioned and configured by the surgeon or assistant personnel, e.g., by scissors if the nature of the drug-eluting matrix and/or drug-eluting device permits, at or near the time the drug-eluting device is to be affixed to the selected anterior spinal plate.

The drug-eluting matrix component of the drug-eluting device can be fabricated from amongst any of the numerous biocompatible materials heretofore known for providing drug-eluting devices. Useful matrices include non-bioresorbable, or non-bioabsorbable, materials and bioresorbable, or bioabsorble, materials. Natural, semi-synthetic and fully synthetic polymers of both types are well known in the art for use as drug-eluting matrices.

Among the useful non-bioresorbable drug-eluting matrices are polyurethanes, silicones (polysiloxanes), polyesters, polyamides, polyolefins such as polyethylene, polypropylene, polyisobutylene and their copolymers, acrylic polymers and copolymers, vinyl halide polymers and copolymers, polyvinyl ethers, polyacrylonitriles, polyvinyl ketones, polyvinyl aromatics such as polystyrene, polyvinyl esters, polycarbonates, polyimides, polyethers, epoxy resins, and the like.

Useful bioresorbable drug-eluting matrices include hydrogels, poly(L-lactic acid), poly(glycolic acid), poly(lactide-co-glycolide), polydioxanone, polyorthoesters, polyanhydrides, and the like.

If desired, the drug-eluting device herein can be provided as a laminate with, e.g., a first layer (the layer closest to the surface of the anterior spinal plate to which the device will be affixed) fabricated from a non-bioresorbable matrix containing one or more elutable drugs and superimposed thereon a second layer of bioresorbable matrix containing the same or different drug(s) as the first layer.

The drug-eluting properties of a drug-eluting matrix, principally the rate of release of its drug component(s) into the surrounding body tissues, is of prime importance. Those skilled in the art employing known procedures can readily select the optimum drug-eluting matrix material for a particular drug or drug combination and drug loading(s).

The selected drug(s) can be incorporated in the drug-eluting matrix during and/or after the formation of the drug-eluting matrix material. The incorporation of drug can be substantially uniform or the drug(s) can be distributed in the drug-eluting matrix in gradient fashion or in distinct zones of concentration employing any of several methods known in the art. Thus, e.g., a greater concentration of drug(s) at or near the exposed surface of the drug-eluting matrix can be made to provide an initially higher concentration of drug(s) in the surrounding tissues followed by a reduction in delivered drug concentration (and perhaps longer term drug delivery as well if desired) as the more interior regions or zones of lower drug concentration within the drug-eluting matrix begin eluting the drug. This gradient or zonal distribution of drug in the drug-eluting matrix can be utilized to initially deliver a higher concentration of one drug in a drug combination followed by later delivery of a higher concentration of another drug in the drug combination.

Useful drug incorporation procedures include combining the selected elutable drug(s) with the precursor(s) of the matrix and thereafter forming the matrix. Thus, in the case of a polymeric matrix, e.g., an open cell polyurethane foam, the drug(s) can be admixed with the precursor reactants (e.g., polyisocyanate and polyol among other components of the polyurethane foam-forming reaction mixture) with the resulting polyurethane foam entraining the drug(s).

Another drug incorporation procedure involves contacting the drug-eluting matrix material with a drug-containing solvent medium which dissolves the matrix and, following evaporation of the solvent(s), leaves the drug(s) in the reconstituted matrix. A similar procedure involves contacting the drug-eluting matrix with a drug-containing swelling agent and allowing the drug(s) to diffuse into the matrix.

When an open cell matrix is used as the drug-eluting vehicle, e.g., the aforementioned polyurethane foam, the desired drug(s) can be incorporated in the matrix by immersion in a suitable aqueous and/or organic solvent solution of the drug(s) followed by draining excess solvent and if desired, drying.

The drug-eluting matrix can also be fashioned from organic and/or inorganic particulate material and drug bonded together in the desired configuration employing a biocompatible bonding or binder material. Examples of a binder material include the resorbable or non-resorbable biomaterials mentioned above. Additional examples of a binder material include those used in pharmaceutical industry such as a polysaccharide material, a cellulose material, a collagen material, a gelatin material, a synthetic bioresorbable polymer, etc.

These and/or other known techniques can also be used to incorporate one or more non-drug materials in the matrix component of the drug-eluting device herein. Among some optional non-drug materials that can be incorporated in the drug-eluting matrix are diluents, carriers, excipients, stabilizers, permeation enhancers, surface active agents, and the like, in known and conventional amounts.

The amounts of elutable drug for incorporation in the drug-eluting matrix herein will depend on a number of factors well understood by those skilled in the art including the nature of the selected drug(s), the nature, amounts and configuration of the selected matrix and the desired profile (rate and duration) of drug release into the surrounding tissues. Again, empirical investigation employing known and conventional procedures can be utilized by those skilled in the art to arrive at an optimum concentration of specific drug(s) for a specific matrix arrangement. The concentration of drug(s) and the drug-eluting profile of the matrix component of the drug-eluting device will be such as to deliver a therapeutically effective concentration of the desired drug(s) for a therapeutically useful duration. Total concentration of deliverable drug can range, e.g., from about 0.1% to about 20%, and preferably about 1% to about 10%, weight percent of the drug-eluting matrix and can provide eluted drug(s) in therapeutically useful amounts for periods ranging e.g., for at least 24 hours and preferably at least 70, 100, 250, 500 or even 750 hours or more. In certain embodiments, the duration of effective drug release can be range from 1 to 6 months.

As previously indicated, the dimensions of the drug-eluting device can vary considerably. Thus, the surface dimensions of the device can be such as to exceed, match or be less than that of the surface of the anterior spinal plate to which it is affixed. By way of illustration, in the case of a cervical plate having an average major surface dimension (e.g., length) of about 25 mm and a minor surface dimension (e.g., width) of about 12 mm, the drug-eluting device can possess a length of from about 5 mm to about 27 mm and a width of from about 2 mm to about 14 mm.

The thickness of the drug-eluting device can influence the rate of drug release from the device and can vary considerably depending on the drug release profile desired. In one embodiment, the thickness of the drug-eluting matrix component of the drug-eluting device can range, e.g., from about 0.1 mm to about 5 mm and preferably from about 0.5 mm to about 2 mm.

The drug(s) selected for incorporation in the drug-eluting device can in their essentially pure and/or concentrated form be a solid material, e.g., a powder, a semi-solid or a liquid of widely varying appearance. The physical properties and characteristic elution rates from a given drug-eluting matrix can be determined by a person of ordinary skill in the art, including when the drug is encased in a dissolvable solid bead or liposome for delayed release of the drug. When desired, a drug can be incorporated in the drug-eluting matrix in both an encapsulated form and a free form via suitable carrier liquids, e.g., solvents, in particular, water, organic solvent(s) or aqueous mixtures of organic solvent(s). In addition, the drug-eluting matrix may optionally contain one or more non-drug materials, e.g., one or more of those previously recited, dissolved, suspended or dispersed therein. It will, of course, be appreciated that when the physical form of the pure and/or concentrated drug is that of a solid or semi-solid, it may be beneficial if at least some portion of the carrier with the drug(s) dissolved, suspended or dispersed therein is retained in the polymer matrix for subsequent delivery of such drug(s) to the surrounding region of tissue.

The drug, or drugs, incorporated in the drug-eluting matrix of the drug-eluting device herein include, interalia, anti-infective agents such as antibiotics, antiseptics, antiviral agents and anti-fungal agents, anti-inflammatory agents, local anesthetics and/or any of numerous other classes of therapeutic agents.

Any antibiotic suitable for use in a human may be used in accordance with various embodiments of the invention. As used herein, "antibiotic" means an antibacterial agent. The antibacterial agent may have bateriostatic and/or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104, the entire contents of which are incorporated by reference herein, may also be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus, Staphlococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that using two or more antimicrobial agents having different mechanisms of action and/or different spectrums of action may be most effective in achieving the desired effect. In one embodiment, a combination of rifampin and minocycline is used, e.g., at a rifampin loading of from about 0.1% to about 20%, preferably from about 1% to about 10%, and a minocyline loading of from about 0.1% to about 20% and preferably from about 1% to about 10%. In another embodiment, rifampin at one of the aforementioned loadings can be combined with clindamycin at a loading of from about 0.1% to about 20% and preferably from about 1% to about 10%.

Any antiseptic suitable for use in a human may be used in accordance with various embodiments of the invention. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the antiseptic(s) selected kill or inhibit the growth of one or more microbe that are associated with infection following surgical implantation of a medical device. Such microbes are recognized by those of ordinary skill in the art and include *Stapholcoccus aureus, Staphlococcus epidermis, Escherichia coli, Pseudomonus auruginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving the desired effect of inhibiting a broad spectrum of potentially infectious microbes and/or drug resistant microbes. In a particular embodiment, a combination of chlorohexidine and silver sulfadiazine is used.

Any antiviral agent suitable for use in a human may be used in accordance with various embodiments of the invention. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

Any anti-fungal agent suitable for use in a human may be used in accordance with various embodiments of the invention. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that viruses will be killed or inhibited, it may be desirable to combine two or more anti-fungal agents. It may also be desirable to combine one or more antiseptics with one or more anti-fungal agent.

Any anti-inflammatory agent suitable for use in a human may be used in accordance with various embodiments of the invention. Non-limiting examples of anti-inflammatory agents include steroids, such as cortisone, hydrocortisone, prednisone, dexamethasone, methyl-prednisilone, an, derivatives thereof; and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Any local anesthetic agent suitable for use in a human may be used in accordance with various embodiments of the invention. Non-limiting examples of local anesthetics agents include lidocaine, prilocaine, mepivicaine, benzocaine, bupivicaine, amethocaine, lignocaine (lidocaine), cocaine, cinchocaine, dibucaine, etidocaine, procaine, veratridine (selective c-fiber blocker) and articaine.

Non-limiting examples of other pharmacological agents that may be used include: beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin; antineoplastic/antiangiogenic agents, such as antimetabolite agents, alkylating agents, cytotoxic antibiotics, vinca alkaloids, mitosis inhibitors, platinum compounds, tissue growth factor inhibitors, cisplatin and etoposide; immunosuppressant agents, such as cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors; anticoagulents, such as heparin and chondroiten sulfate; platelet inhibitors such as ticlopidine; vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; thrombolytic agents, such as stretokinase, urokinase and tissue plasminogin activators; analgesics and antipyretics, such as the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone; and, antiproliferative agents such as QP-2 (taxol), paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, and probucol; and combinations and/or derivatives thereof.

The following example is illustrative of the manufacture of the drug-eluting device of the anterior spinal plate of the invention.

EXAMPLE

An adhesive-backed sheet made of silicone elastomer and silicone adhesive with a length of 20 mm, a width of 10 mm, and a thickness of 1 mm is used as a drug-eluting device for an anterior cervical plate. The sheet contains 4 weight percent of Rifampin and 6 weight percent of Minocycline. Alternately, the sheath contains 4 weight percent Rifampin and 6 weight percent Clindamycin. The drugs can be incorporated into the silicone before, during or after the curing of the silicone. In one example, the drugs can be mixed into a room temperature vulcanized (RTV) silicone elastomer prior to molding or casting. Alternately, the drugs may be incorporated into the silicone elastomer sheet via a solvent-swelling method. The sheet loaded with antimicrobial drugs is sterilized with ethylene oxide gas and supplied to the operating room in sterile packaging. The sheet is affixed to the anterior cervical plate before, during or after implantation of the plate in order to provide the implanted tissue areas with locally released antibiotics.

Methods of affixing the drug-eluting device of the foregoing example are illustrated in FIGS. 1-4.

Figure 1:
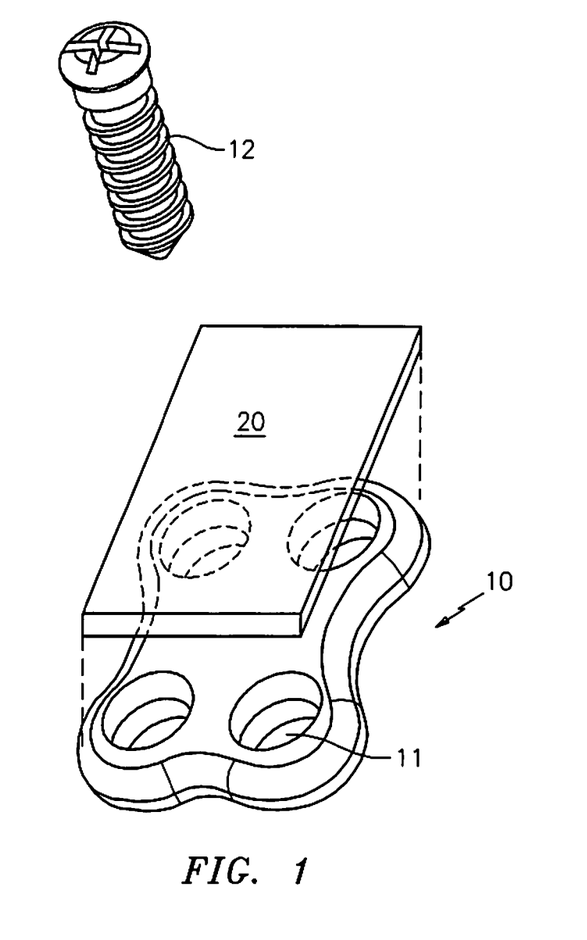
FIG. 1 is a perspective view of one embodiment of an anterior spinal plate and a preformed drug-eluting device of this invention about to be affixed to the plate.

As shown in FIG. 1, an anterior spinal plate 10 of known design measuring an average of about 30 mm in length, 12 mm in width and 2.5 mm in thickness and fabricated from any suitable material, e.g., metal, bioresorbable polymer, non-bioresorbable polymer, ceramic, inorganic/organic composite, etc., features openings 11 for reviewing each of screws 12 for securing plate 10 to spinal bone at a desired location. As anterior spinal plate 10 is being screwed to the spinal bone, rectangular-shaped drug-eluting device 20 fabricated as described above is simultaneously affixed to the surface of the plate by the same screws 12.

Figure 2:
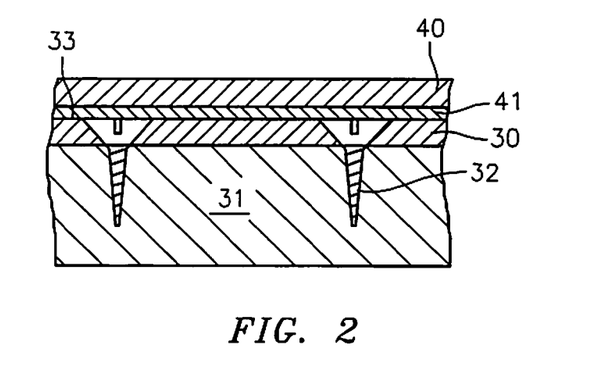
FIG. 2 is a side elevation view of one embodiment of anterior spinal plate of this invention secured to spinal bone, the plate having the drug-eluting device affixed thereto via biocompatible adhesive.

In the embodiment of installed anterior spinal plate shown in side elevation view in FIG. 2, anterior plate 30 secured to spinal bone surface 31 via screws 32 possesses drug-eluting device 40 affixed to surface 33 of plate 30 by a layer of biocompatible adhesive 41 previously applied to a surface of device 40. Biocompatible adhesives include cyanoacrylate, epoxy, silicone, acrylics, polyvinyl alcohol, polyurethane, albumin, collagen, etc. and mixtures thereof.

Figure 3:
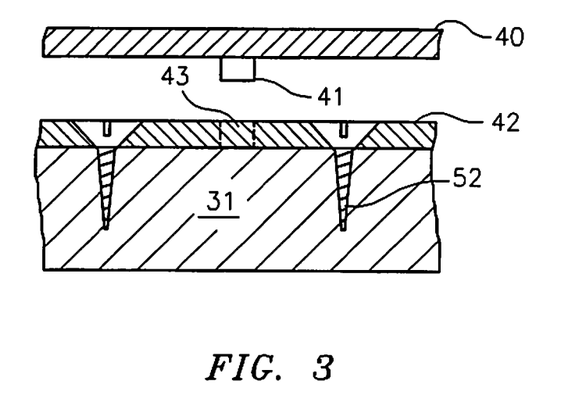
FIG. 3 is a side elevation view of one embodiment of anterior plate and the snap fit/pressure fit.

In the embodiment of installed anterior spinal plate shown in side elevation view FIG. 3, anterior plate 42 secured to spinal bone surface 31 via screws 32 further comprises a cavity 43. FIG. 3 also shows a drug eluting matrix 40 having an extension 41 configured to pressure fit/friction fit into the cavity 43 on the secured anterior plate.

Figure 4:
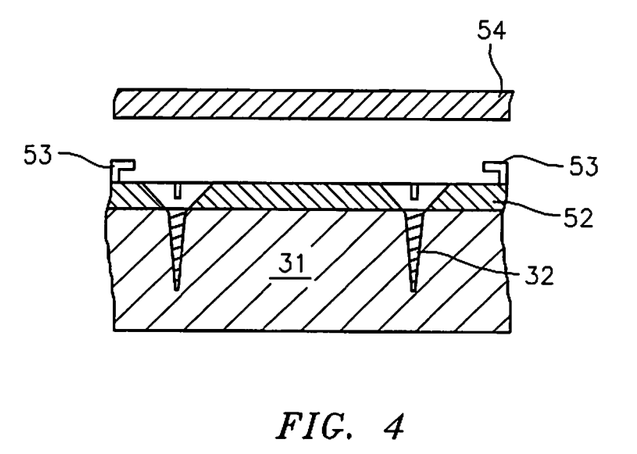
FIG. 4 is a side elevation view of one embodiment of anterior plate having locking elements configured to engage the drug-eluting matrix.

FIG. 4 shows an alternative embodiment of an anterior plate 52 secured to spinal bone surface 31 via screw 32 further comprising locking elements such as flanges 53 positioned on the edges of the anterior plate 52. In this embodiment, the drug-eluting matrix 54 is held in place by flange 53 (or multiple flanges). The flange 53 can be configured so as to lock into or pressure fitted with the drug-eluting matrix 54.

Other configurations are also possible, for example, configurations that use the above-discussed structural and adhesive components to attach the drug-eluting matrix to the anterior spinal plate of the invention fall within the invention.

While the invention has been illustrated and described in detail the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A drug-eluting device comprising a drug-eluting biocompatible matrix comprising a layer of a bioresorbable polymer and at least one antibacterial elutable drug comprising clindamycin at a level of from 1 to about 20 weight percent of the drug-eluting biocompatible matrix in combination with rifampin at a level of from 1 to about 20 weight percent of the drug-eluting biocompatible matrix, and minocycline at a level of from 1 to about 20 weight percent of the drug-eluting biocompatible matrix, said device comprising at least one locking element configured to attach with an anterior spinal plate, wherein the matrix comprises a non-bioresorbable layer disposed in between the plate and the bioresorbable layer and each layer comprises distinct zones of concentration within the matrix with the drugs clindamycin, rifampin and minocycline.

2. The drug-eluting device of claim 1, wherein said at least one locking element includes an elastomeric material configured to engage a surface of the anterior spinal plate in a snug fit arrangement.

3. The drug-eluting device of claim 1, wherein the drug-eluting matrix comprises at least one semi-synthetic, or fully synthetic polymer.

4. The drug-eluting device of claim 3, wherein the semi-synthetic or fully synthetic polymer is selected from the group consisting of silicone, polyurethane, silicone-polyurethane copolymers, polyethylene, polypropylene, polyester, polyaryletherketone, polyimide, polyetherimide, polyamide, polysulfone and combinations thereof.

5. The drug-eluting device of claim 1, wherein the bioresorbable polymer is selected from the group consisting of hydrogel, polylactide, polyglycolide, copolymers of polylactide and polyglycolide, polycaprolactone, polyorthoester and combinations thereof.

6. The drug-eluting device of claim 1, wherein said locking element is selected from the group consisting of tabs, sutures, staples, anchors, pins, screws, flexible or elastic structures configured to snap-fit or pressure-fit the drug-eluting device to the anterior spinal plate.

7. The drug-eluting device of claim 1, wherein at least a portion of a surface of the drug-eluting device comprises a layer of biocompatible adhesive positioned to securely attach the drug-eluting device to at least a portion of a tissue exposed surface of the anterior spinal plate.

8. The drug-eluting device of claim 7, wherein the biocompatible adhesive comprises at least one material selected from the group consisting of cyanoacrylate, epoxy, silicone, acrylics, polyvinyl alcohol, polyurethane, polysaccharide, albumin, collagen and combinations thereof.

9. The drug-eluting device of claim 1, wherein the drug-eluting device is configured to be attached to the anterior spinal plate having one or more screws used for securing the anterior spinal plate to spinal bone.

10. The drug-eluting device of claim 1, wherein the drug-eluting matrix comprises a hydrogel selected from the group consisting of a polyvinyl alcohol, a polyacrylic acid, a polyarylamide, a poly(acrylonitrile-acrylic acid), a polyurethane, a polyethylene glycol, a poly(N-vinyl-2-pyrrolidone), a gelatin, a collagen, a polysaccharide, a cellulose, and combinations thereof.

11. The drug-eluting device of claim 1, wherein the bioresorbable polymer comprises polycaprolactone.

12. The drug-eluting device of claim 1, wherein the at least one elutable drug is encased in liposomes for delayed release of the at least one elutable drug.

13. The drug-eluting device of claim 1, wherein the antibacterial consists of clindamycin, rifampin and minocycline.

14. A spinal implant kit comprising: a) an anterior spinal plate; and, b) at least one preformed drug-eluting device fabricated from a drug-eluting matrix comprising a layer of a bioresorbable polymer and at least one antibacterial elutable drug comprising clindamycin at a level of from 1 to about 20 weight percent of the drug-eluting matrix in combination with rifampin at a level of from 1 to about 20 weight percent of the drug-eluting matrix, and minocycline at a level of from 1 to about 20 weight percent of the drug-eluting biocompatible matrix, said device comprising at least one locking element configured to attach with said anterior spinal plate, wherein the matrix comprises a non-bioresorbable layer disposed in between the plate and the bioresorbable layer and each layer comprises distinct zones of concentration within the matrix with the drugs clindamycin, rifampin and minocycline.

15. A method for surgically installing an anterior spinal plate in a body which comprises surgically installing an anterior spinal plate in the body of a patient and affixing to at least a portion of a surface of the plate at least one preformed drug-eluting device fabricated from a drug-eluting biocompatible matrix comprising a layer of a bioresorbable polymer and at least one antibacterial elutable drug comprising clindamycin at a level of from 1 to about 20 weight percent of the drug-eluting biocompatible matrix in combination with rifampin at a level of from 1 to about 20 weight percent of the drug-eluting biocompatible matrix, and minocycline at a level of from 1 to about 20 weight percent of the drug-eluting biocompatible matrix, said device comprising at least one locking element configured to attach with said anterior spinal plate, wherein the matrix comprises a non-bioresorbable layer disposed in between the plate and the bioresorbable layer and each layer comprises distinct zones of concentration within the matrix with the drugs clindamycin, rifampin and minocycline, the affixing step being carried out prior to, during or following the installing step.

16. The method of claim 15, wherein the preformed drug-eluting device is affixed to the anterior spinal plate by biocompatible adhesive, one or more screws, pressure fit or is a stretchable structure that is engagedly fitted to some portion of the plate.

17. The method of claim 16, wherein the biocompatible adhesive is present on at least a portion of a surface of the drug-eluting device to be contacted with a surface of the anterior spinal plate.

* * * * *